(12) United States Patent
Leo et al.

(10) Patent No.: US 6,667,046 B2
(45) Date of Patent: *Dec. 23, 2003

(54) COSMETIC WATER-IN-SILICONE EMULSION

(75) Inventors: Claudia Leo, São Paulo-SP (BR); Luciana Gandini, São Paulo-SP (BR)

(73) Assignee: Industria e Comercio de Cosmeticos Natura Ltda, Itapecerica da Serra-SP (BR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/437,150

(22) Filed: Nov. 10, 1999

(65) Prior Publication Data

US 2002/0192244 A1 Dec. 19, 2002

(30) Foreign Application Priority Data

Nov. 10, 1998 (BR) .............................................. 9804595

(51) Int. Cl.$^7$ ............................. A61K 7/00; A61K 7/42; A61K 7/06; A61K 7/11; A61K 7/075
(52) U.S. Cl. ....................... 424/401; 424/59; 424/70.12; 424/70.19; 514/937; 516/21; 516/22; 516/23
(58) Field of Search ........................ 424/401, 59, 70.12, 424/70.19; 514/937; 516/23, 22, 21

(56) References Cited

U.S. PATENT DOCUMENTS

| | | | | |
|---|---|---|---|---|
| 5,306,486 A | * | 4/1994 | McCook et al. | 424/59 |
| 5,665,368 A | * | 9/1997 | Lentini et al. | 424/401 |
| 5,691,380 A | * | 11/1997 | Mason et al. | 514/562 |
| 5,733,535 A | * | 3/1998 | Hollingshead et al. | 424/65 |
| 5,939,054 A | * | 8/1999 | Msika et al. | 424/59 |
| 5,939,082 A | * | 8/1999 | Oblong et al. | 424/401 |
| 5,997,887 A | * | 12/1999 | Ha et al. | 424/401 |
| 6,083,491 A | * | 7/2000 | Mellul et al. | 424/63 |
| 6,132,739 A | * | 10/2000 | Leverett | 424/401 |
| 6,294,186 B1 | * | 9/2001 | Beerse et al. | 424/401 |

* cited by examiner

*Primary Examiner*—Michael G. Hartley
*Assistant Examiner*—Marina Lamm
(74) *Attorney, Agent, or Firm*—Smith, Gambrell & Russell

(57) ABSTRACT

The present invention refers to water-in-silicone type cosmetic emulsion which comprises particulate solid cosmetic components and includes as emulsifying system an association of a primary emulsifier selected from the group comprising copoliols and a secondary emulsifier selected from lipophilic stearic acids, wherein such particulate solid cosmetic components have a maximum particle size and a degree of repellence among the particles and the environment in which they are dispersed sufficient to guarantee their stability in relation to the environment in which they are dispersed.

8 Claims, No Drawings

COSMETIC WATER-IN-SILICONE EMULSION

FIELD OF THE INVENTION

The present invention relates to a water-in-silicone type cosmetic emulsion, stable in the presence of particulate materials which provides desirable cosmetic properties for such a product.

BACKGROUND OF THE INVENTION

Patent application JP 9278626 describes a process for the production of raw material consisting of a sequence of polymerization and catalytic reactions resulting in a final product in the form of a basic emulsion lacking cosmetic properties, acting in this way as a basic component in the production of a cosmetic product.

Patent application EP 600445 discusses a cosmetic composition of the water-in-oil type containing pigment in its internal phase. In its turn U.S. Pat. No. 5,389,363 describes a product to be used specifically as mascara for eyelashes containing silicone, although it lacks compounds for cosmetic treatment such as physical filters and sensorial modifiers.

Patent application EP 0709083 teaches the prepration of a generic cosmetic product which effect is the non transfer thereof to clothes and to objects. However such a product lacks properties for cosmetic use and for treatment, which could make it a more acceptable product to the consumer.

Therefore, according to what is known from the state of the art, in the attempts of incorporating cosmetic compounds in the form of powder such as physical filters, sun protectants and other cosmetic compositions, into various emulsions such as the oil-in-water type and especially as the water-in-silicone type, which sensorial effect of the resulting product is quite agreeable, such incorporation causes the destabilization of the emulsion, making the product infeasible.

OBJECTIVES OF THE INVENTION

Consequently the objective of the present invention is to provide a cosmetic composition in the form of a water-in-silicone emulsion that overcomes the disadvantages of known solutions of the previous art in relation to stability and to other factors such as sensorial effect and also of competitive cost.

SUMMARY OF THE INVENTION

The present invention refers to a water-in-silicone type cosmetic emulsion which contains solid cosmetic particulate components and comprises, as an emulsifying system, the association of a primary emulsifier selected form the group which comprises copoliols and a secondary emulsifier selected from lipophyllic stearic acids, wherein the above mentioned solid cosmetic particulate components present a maximum particle size and a degree of repellence between the particles which are sufficient to guarantee its stability in relation to the environment in which they are dispersed.

DETAILED DESCRIPTION OF THE INVENTION

According to the present invention, the water-in-silicone emulsion that comprises a mixture of silicones which comprise the external phase of the composition, is stable in the presence of particulate materials bearing desirable cosmetic properties in this product such as physical filters, for example titanium dioxide, and others which contribute to the improvement of the cosmetic properties, such as sensorial modifying particles, for example Nylon 12.

The emulsion as herein defined provides the advantage of enabling the final product to stay on the skin for a longer time, which prolongs the action of particulate materials bearing desirable cosmetic properties in such a product.

Another advantage is that the stability achieved in this way also allows the yet unknown inclusion of so-called "treatment compounds" in this type of emulsion, such as anti-radical agents like vitamin E, in association or not with proanthocyanidins (OPC).

According to the invention the problem of incorporating cosmetic compounds on the form of powder into a water-in-silicone emulsion is solved by selecting an adequate emulsifying system and by the size of the particles.

According to the invention, such a mixture remains stable even in the presence of said powders when the emulsifying system comprises the association of a primary emulsifier and a secondary emulsifier, the first selected from the family of copoliols, preferably cetyl copoliol dimethicone and the second being selected from lipophyllic stearic acids, preferably polyglycerol 4 isostearate, as well as the selection of particles considering their maximum size and degree of repellence amongst the particles in relation to the environment in which it is dispersed.

In the case of titanium dioxide, for example, bearing a positive charge and dispersed in such an emulsion, the stabilization of the emulsion it was surprisingly noticed with a particle size of less than 15 nanometers.

When the particle to be included is Nylon 12, which carries a positive charge in this emulsion, the stabilization of the emulsion was surprisingly noticed with a particle size of less than 10 microns. The inclusion of Nylon 12 in greater proportions is effected in order to obtain a cosmetic base with an opaque effect.

It must be noted that in the case of the present water-in-silicone emulsion, the particulate materials (such as pigments) are dispersed in its external phase, which provides advantages in relation to other compositions already known in the current state of the art, in which the pigments are dispersed in the internal phase (for example, EP 600,445).

The emulsifying system used in the present invention is normally employed in the range from 3.0 to 5.0%, by weight, based on the total weight of the emulsion.

In addition to the components already mentioned above, the emulsion according to the invention may contain other ingredients conventionally used in this type of composition, such as softeners, preservatives, stabilizers and fragrances. Further advantages of the present emulsion arise from the fact that it allows the inclusion of perfluor coated pigments which have lipophobic and hydrophobic properties, shows treatment benefits with sun protective factor, provides protection against the action of free radicals and the maintenance of hydration, as well as the fact that the emulsifying system used allows stable emulsions to be obtained without requiring the presence of oils and waxes, and that it is an alcohol-free system.

Preferably, the emulsion according to the invention comprises the following chemical composition (all percentages being defined in weight, based on the total weight of the composition):

3.0 to 5.0% emulsifying system 1.8 to 31.0%, softeners (for instance, esters and silicones, whether volatile or not)

1.0 to 6.0% of film forming agents (high molecular weight silicone resin)

0.5 to 17.0% of sensorial modifier (for instance, synthetic polyamide polymer with average particle size of 10 μm)

2.5 to 7.0% of pigments treated with perfluoralkylphosphate about 7.0 to 10.0% of treatment agents (such as ultrafine titanium dioxide—15 nm; 0.10 to 0.60% of glycospheres and grape seed extract associated with vitamin E; 0.1 to 6.0% of moisturizing agents, such as microspheres of sea collagen and glycerin)

in addition to preservatives, stabilisers and fragrance.

The association of treatment benefits obtained with long-duration cosmetic compositions, such as the one defined by the present invention, promotes the permanence of the protection agents for a longer period. Moreover, it prolongs the effect of the makeup when applied on the skin.

The following advantages may, therefore, be listed as a consequence of the surprising results obtained with the present invention:

extended duration of the composition allows the maintenance of the treatment benefits for a longer time, in addition to maintaining the aspect of the makeup skin during this same extended period;

the presence of silicones in the external phase promotes a pleasant, non-oily, non-fatty sensorial effect.

the water-in-silicone emulsion, besides providing excellent sensorial characteristics, proves to be water resistant, through the formation of a protective film, and shows uniformity, good spreading conditions and durability;

the presence of the high molecular weight silicone resin allows the formation of a highly durable and resistant film on the skin, after the evaporation of the volatile components, thus avoiding the transfer of the product when applied to other surfaces;

the final result effects of the makeup may change from opaque to natural, depending on the concentration of the solid materials used;

when present, perfluor coated pigments, allow a perfect homogeneity of the product when it is applied on the surface of the skin with no agglomerates. In addition to increasing the resistance and duration of the composition, the presence of titanium dioxide, for instance, with a particle size in the order of 15 nanometers allows to graduate the desired sun protective factor, for instance SPF 8, with physical filter, diminishing the risk of irritation caused by chemical filters. The reduced particle size guarantees the product transparency;

when the emulsion also contains glycerin and collagen microspheres, it guarantees that the natural moisture of the skin is maintained;

if there is an association of Vitamin E and OPC glycospheres, a protection against the action of the free radicals is also obtained;

the composition is comfortable when applied to the skin and is made of non-toxic and non-irritant components.

The illustrative examples presented below will better describe the present invention. However, the data given in the examples refer merely to some embodiments of the present invention, and should not be taken in any way to limit the scope thereof.

EXAMPLES

| Component | Proportion (% by Weigh) |
|---|---|
| 1) Water-in-Silicone Type Emulsion of Natural Effect | |
| Cyclomethicone | About 20,00 |
| Oily Vitamin E | About 0,20 |
| Cyclo/trimethilsiloxisilicate | About 2,50 |
| Cyclomethicone/dimethilconol | About 2,5 |
| Isopropyl palmitate | About 1,75 |
| Ultrafine Titanium dioxide (15 nm) | About 7,00 |
| Pigments | About 4,00 |
| Nylon 12 | About 0,70 |
| Cetil dimethicone copoliol | About 3,00 |
| Triglycerol Isostearate | About 1,25 |
| Water | QS for 100% |
| Sodium Chloride | 0,50 |
| Bi-distilled white glycerin | About 3,10 |
| OPC glycospheres | About 0,25 |
| Sea origin collagen microspheres | About 0,20 |
| Preservative GD-700 | Up to 0,50 |
| Compact O5 essence | Up to 0,10 |
| 1) Water-in-Silicone Type Emulsion with Opaque Effect ("Matt") | |
| Cyclomethicone | About 20,00 |
| Oily Vitamin E | About 0,25 |
| Cyclo/trimethilsiloxisilicate | About 4,50 |
| Cyclomethicone/dimethilconol | About 2,50 |
| Isopropyl palmitate | About 3,50 |
| Ultrafine Titanium dioxide (15 nm) | About 7,00 |
| Pigments | About 7,00 |
| Nylon 12 | About 15,50 |
| Cetil dimethicone copoliol | About 2,50 |
| Triglycerol Isostearate | About 0,50 |
| Water | QS for 100% |
| Sodium Chloride | 0,50 |
| Bi-distilled white glycerin | About 4,50 |
| OPC glycospheres | About 0,28 |
| Sea origin collagen microspheres | About 0,50 |
| Preservative GD-700 | Up to 0,50 |
| Compact O5 essence | Up to 0,10 |

What is claimed is:

1. A cosmetic water-in-silicone emulsion comprising solid particulate cosmetic components and, an association of a primary emulsifier comprising:
   a copolyol, and
   a secondary emulsifier comprising a lipophilic stearic acid,
   wherein said solid particulate cosmetic components are titanium dioxide particles having a particle size of below 15 nanometers and a positive charge which induces a degree of repellence among the particles and the environment in which the particles are dispersed sufficient to guarantee their stability in relation to the environment in which they are dispersed.

2. A cosmetic water-in-silicone emulsion according to claim 1, wherein the primary emulsifier comprises cetyl dimethicone copolyol and the secondary emulsifier is polyglyceryl-4-isostearate.

3. A cosmetic water-in-silicone emulsion according to claim 1, wherein the emulsifying system is present in a proportion in the range of 3.0 to 5.0%, by weight, based on the total weight of the composition.

4. A cosmetic water-in-silicone emulsion according to claim 2, wherein the emulsifying system is present in a proportion in the range of 3.0 to 5.0%, by weight, based on the total weight of the composition.

5. A cosmetic water-in-silicone emulsion comprising
solid particulate cosmetic components and,
an association of a primary emulsifier comprising:
   a copolyol, and
   a secondary emulsifier comprising a lipophilic stearic acid,
   wherein said solid particulate cosmetic components are Nylon 12 particles having a particle size below 10 microns and a positive charge which induces a degree of repellence among the particles and the environment in which the particles are dispersed sufficient to guarantee their stability in relation to the environment in which they are dispersed.

6. A cosmetic water-in-silicone emulsion according to claim 5, wherein the primary emulsifier comprises cetyl dimethicone copolyol and the secondary emulsifier is polyglyceryl-4-isostearate.

7. A cosmetic water-in-silicone emulsion according to claim 5, wherein the emulsifying system is present in a proportion in the range of 3.0 to 5.0%, by weight, based on the total weight of the composition.

8. A cosmetic water-in-silicone emulsion according to claim 6, wherein the emulsifying system is present in a proportion in the range of 3.0 to 5.0%, by weight, based on the total weight of the composition.

* * * * *